United States Patent [19]

Ferguson et al.

[11] Patent Number: 5,726,899
[45] Date of Patent: Mar. 10, 1998

[54] METHOD OF INDICATING FAT CONTENT OF A FOOD PRODUCT

[75] Inventors: Karen Ferguson, 17012 Triple Butte Cir., Colbert, Wash. 99005; David Rice, Spokane, Wash.

[73] Assignee: Karen Ferguson, Colbert, Wash.

[21] Appl. No.: 513,444

[22] Filed: Aug. 10, 1995

[51] Int. Cl.$^6$ .................................................. G06F 17/60
[52] U.S. Cl. .................. 364/479.01; 364/479.03; 364/479.05; 364/479.11
[58] Field of Search ............... 426/87, 383; 156/277, 156/244.16; 33/1 B, 1 SB; 221/1, 2, 5, 7-9; 434/127, 113, 114; 53/415; 235/375, 376, 380, 383, 432; 283/117, 115; 364/479.01, 479.03-479.06, 479.11, 12, 464.1, 464.11, 464.19, 464.24, 464.26, 413.01, 413.02, 413.29, 550, 551.01, 567, 568, 496-499; 395/223, 24; 73/53.02, 65.7

[56] References Cited

U.S. PATENT DOCUMENTS

| | | | |
|---|---|---|---|
| 5,412,564 | 5/1995 | Ecer | 364/413.29 |
| 5,454,721 | 10/1995 | Kuch | 434/127 |
| 5,475,929 | 12/1995 | Yancey | 33/1 SB |
| 5,478,989 | 12/1995 | Shepley | 235/375 |
| 5,558,742 | 9/1996 | Kiefer | 156/244.16 |

OTHER PUBLICATIONS

Brochure, *The M-Fit Grocery Shopping Guide*, Nelda Mercer, M.S., R.D. et al., pp. 191–192. (No date).
Brochure, *the MedSport T-Fit Shelf Labeling Program—it's the easy way to make healthy food choices!* (No date).
Newspaper Article, *Connection—"Shelf talker" makes it easier to find good stuff.* The Ann Arbor News, Feb. 11, 1992.
Newspaper Article, *People & Community—Labels Guide Shoppers to healthy Choices,* Petroskey News–Review, Mar. 7, 1995.
Newspaper Article, *Why We Got Involved In The M-Fit Program,* Michigan Food News, May 1994, p. 14.

*Primary Examiner*—Emanuel T. Voeltz
*Assistant Examiner*—Hal D. Wachsman
*Attorney, Agent, or Firm*—Wells, St. John, Roberts, Gregory & Matkin, P.S.

[57] ABSTRACT

A method of indicating fat content of a food product, including determining fat grams for the product, and calories per serving for the product; calculating, based on the determined fat grams for the product and the determined calories per serving for the product, fat percentage by calories for the product; and generating a label displaying non-alphanumeric graphical indicia indicating fat percentage by calories for the product.

3 Claims, 4 Drawing Sheets

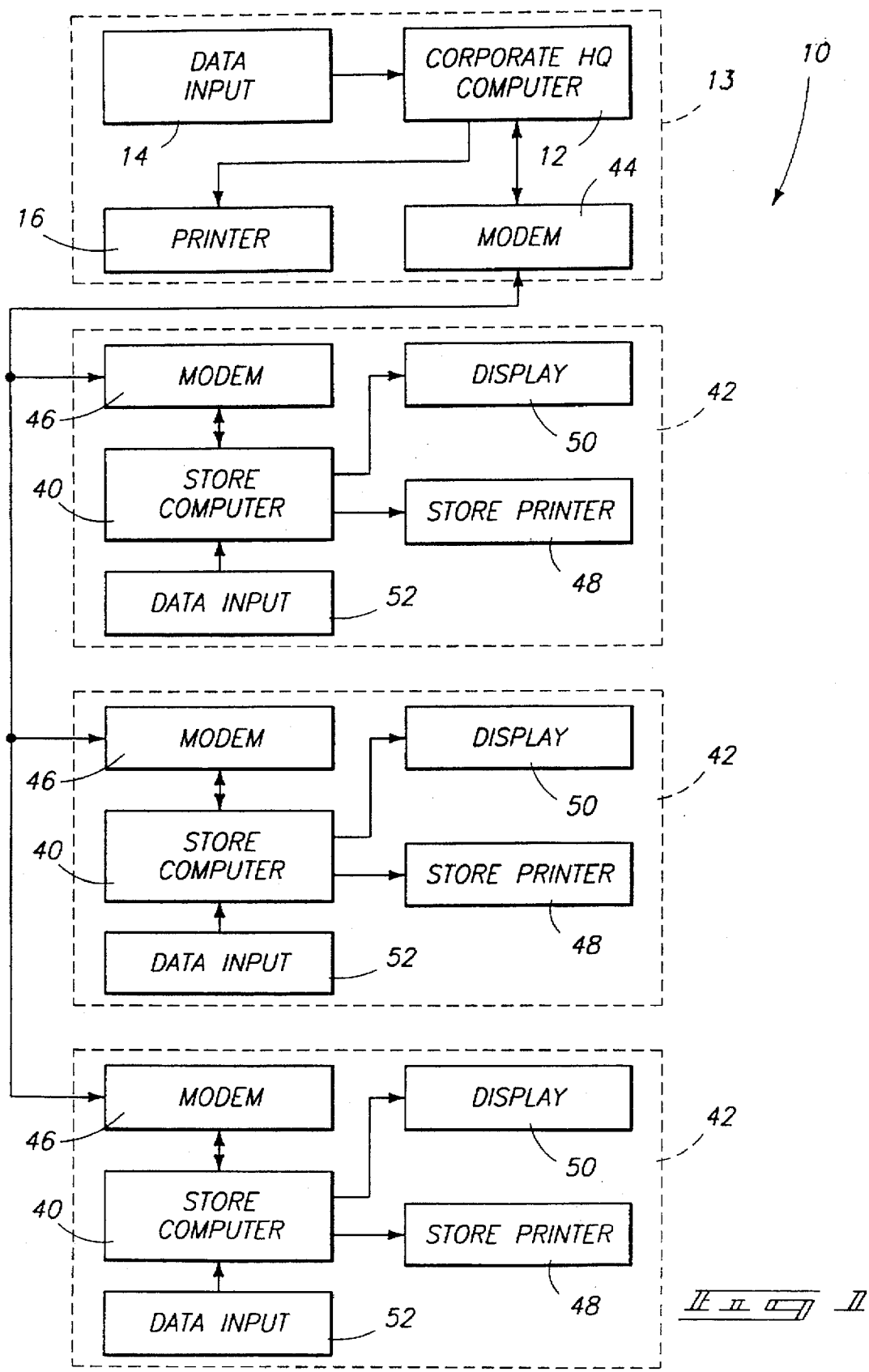

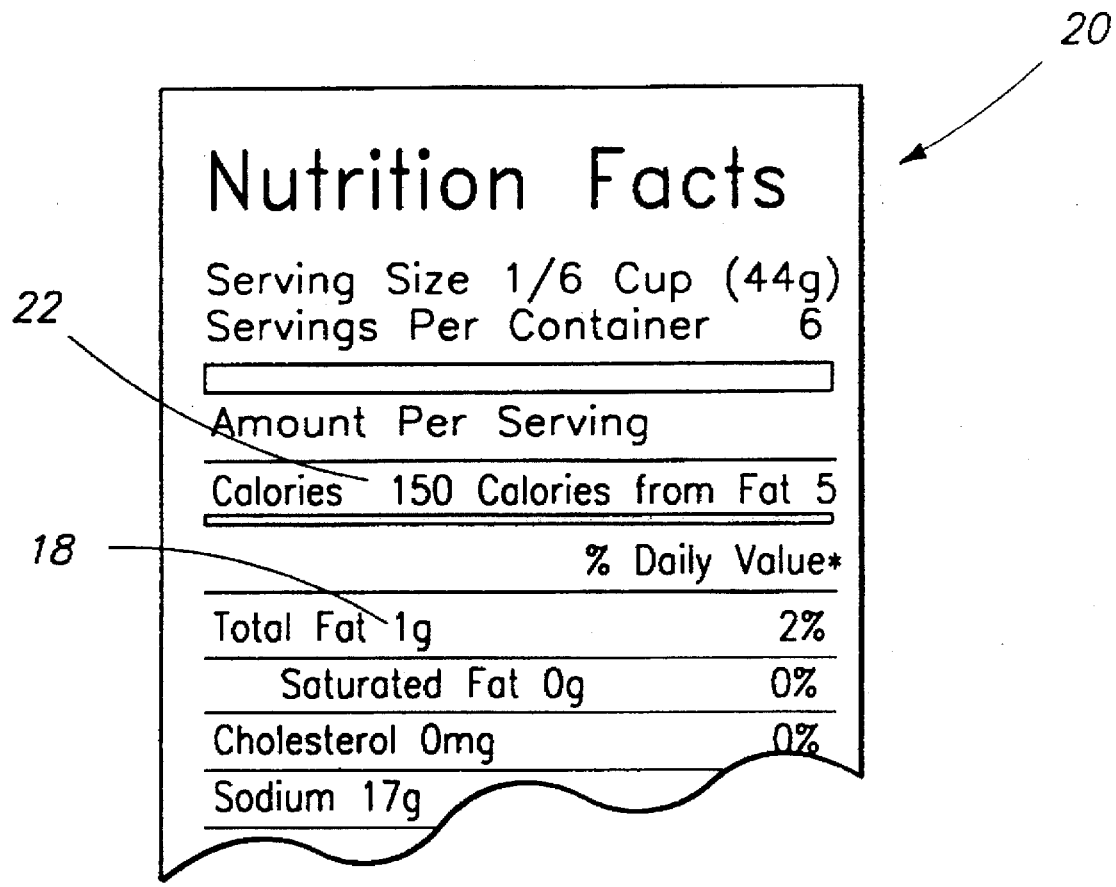

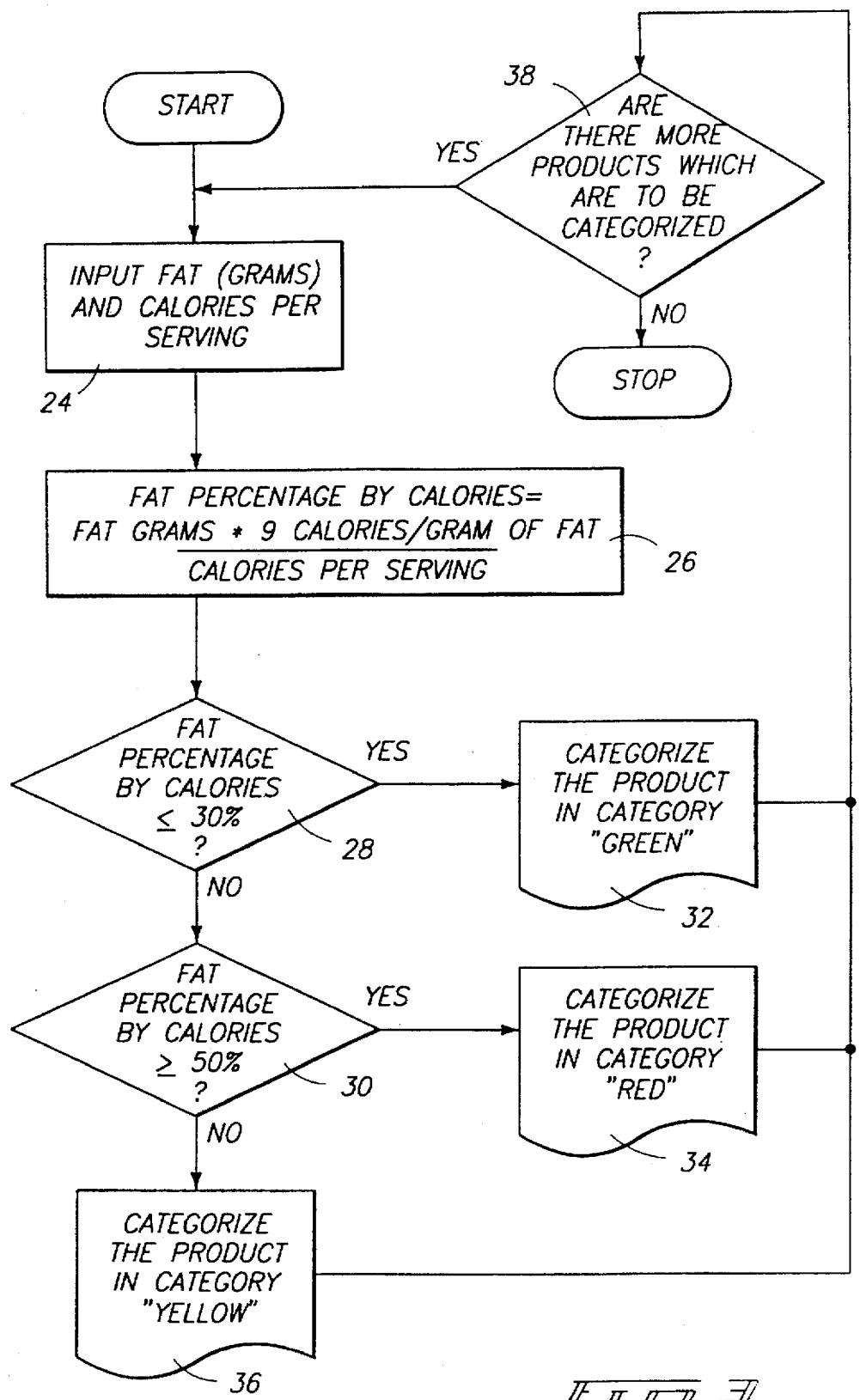

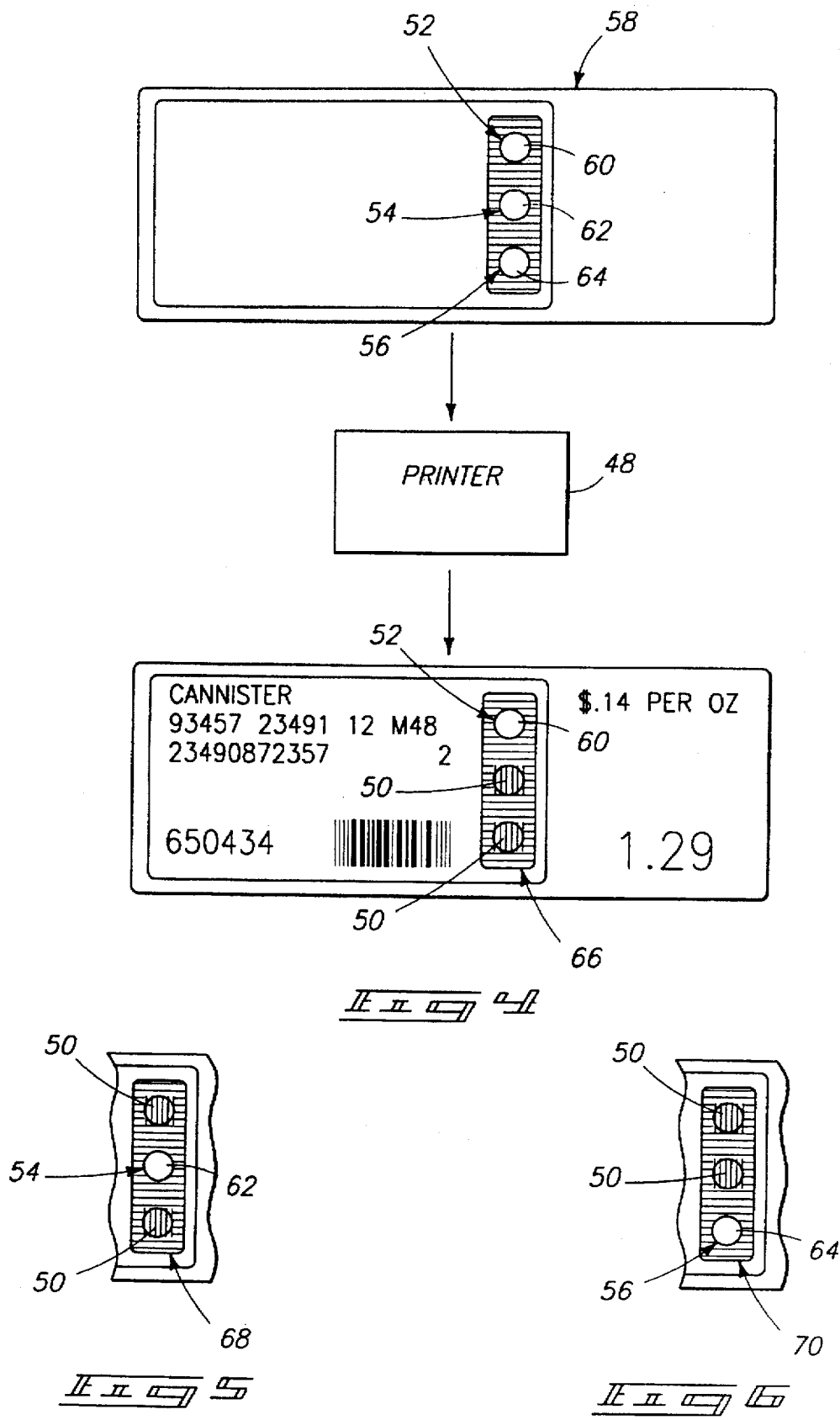

METHOD OF INDICATING FAT CONTENT OF A FOOD PRODUCT

TECHNICAL FIELD

The invention relates to methods of indicating fat content of food.

BACKGROUND OF THE INVENTION

It is known to provide nutritional fact labels on food products. Uniform nutritional fact labels have been mandated by the Nutrition Labeling Education Act (NLEA). These labels have greatly assisted consumers in determining the nutritional value of a food product. Because the nutritional labels are uniform, and all contain the same information, it is relatively easy for consumers to compare competing items and to evaluate nutritional value.

Two of the helpful components of the NLEA are the items: Total fat grams and fat calories. Even though simple arithmetic needs to be done to determine the fat percentage by servings, consumers are unlikely to do the arithmetic. In other words, they are unlikely to figure a low-fat percentage based on the recommended U.S. Dietary Guidelines. Similarly, consumers cannot make quick and easy distinctions between fat content of similar products located in the supermarket aisles.

BRIEF DESCRIPTION OF THE DRAWINGS

Preferred embodiments of the invention are described below with reference to the accompanying drawings, which are briefly described below.

FIG. 1 is a block diagram illustrating a system employed in practicing one embodiment of the invention.

FIG. 2 illustrates a nutrition fact label.

FIG. 3 is a flow chart illustrating logic carried out by the system shown in FIG. 1 to categorize products.

FIG. 4 illustrates how a label indicating the category of a product is produced.

FIGS. 5 and 6 illustrate alternative labels.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

The invention provides a method of indicating fat content of a food product, the method comprising determining fat grams for the product, and calories per serving for the product; calculating, based on the determined fat grams for the product and the determined calories per serving for the product, fat percentage by calories for the product; and generating a label displaying non-alphanumeric graphical indicia indicating fat percentage by calories for the product.

FIG. 1 illustrates a system 10 employed in practicing one embodiment of the invention.

The system 10 includes a corporate headquarters computer 12 having a computer program that associates Universal Product Code (UPC) information with the product. The computer 12 is located in a corporate headquarters 13. The computer 12 is a computer of the type that normally already exists in a headquarters of a supermarket chain and that stores UPC information for food products carried by the chain. For example, in one embodiment of the invention, the computer 12 is a mainframe computer.

The system 10 further includes a data input device 14, such as a keypad, touch screen, scanner, or other appropriate input device, in communication with the computer 12, and includes a printer 16 in communication with the computer 12. The data input device 14 is used to input the UPC information and pricing information for products into the computer 12. The data input device 14 is also used to input nutritional information for a product, the nutritional information including separate entries for information required for a nutrition fact label of the type mandated by the National Labeling Education Act, which information includes an entry for fat grams, and an entry for calories per serving.

The computer 12 includes a processor which performs logic, such as a software program or hardwired logic, that receives as inputs total fat (in grams) and calories per serving for a product, and that determines fat percentage by calories for the product. The total fat (in grams) for a product is the information shown in a location 18 on a nutrition fact label 20 (FIG. 2). The calories per serving for a product is the information shown in a location 22 on the nutrition fact label 20 (FIG. 2).

The logic carried out by the processor is illustrated in FIG. 3.

In step 24, inputs are read for a food product. More particularly, fat grams, and calories per serving are input for the product. After performing step 24, the processor proceeds to step 26.

In step 26, fat percentage by calories for the product is calculated using the following formula:

$$\text{fat percentage by calories} = \frac{(\text{fat grams}) \times (9 \text{ calories per gram of fat})}{\text{calories per serving}}$$

After performing step 26, the processor proceeds to step 28.

In step 28, a determination is made whether the calculated fat percentage by calories for the product is less than or equal to a predetermined threshold. If so, the processor proceeds to step 32; if not, the processor proceeds to step 30. In the illustrated embodiment, the threshold in step 28 is 30 percent. In alternative embodiments, other thresholds indicative of low fat can be employed in step 28.

In step 30, a determination is made whether the calculated fat percentage by calories for the product is greater than or equal to a predetermined threshold. If so, the processor proceeds to step 34; if not, the processor proceeds to step 36. In the illustrated embodiment, the threshold in step 30 is 50 percent. In alternative embodiments, other thresholds indicative of high fat can be employed in step 30.

In step 32, the product is categorized as belonging in a green (low fat) category. More particularly, the green category is associated with the UPC in the computer 12 for this product. After performing step 32, the processor proceeds to step 38.

In step 34, the product is categorized as belonging in a red (high fat) category. More particularly, the red category is associated with the UPC in the computer 12 for this product. After performing step 32, the processor proceeds to step 38.

In step 36, the product is categorized as belonging in a yellow (intermediate fat) category. More particularly, the yellow category is associated with the UPC in the computer 12 for this product. After performing step 32, the processor proceeds to step 38.

The system 10 further comprises a plurality of store computers 40 in various supermarket stores 42. At least one computer 40 is located in each store 42. The stores 42 are spread across a city or larger geographic region. The stores 42, along with the corporate headquarters 13, define a chain of stores.

The computers 40 are computers of the type that normally exist in supermarket stores and store UPC information for products sold by the store. While other types of computers can be employed, in one embodiment the computers 40 are UNIX machines. The corporate headquarters computer 12 periodically communicates with the store computers 40 to update UPC information and to transmit category information for each product indicating whether the product belongs in the red, green or yellow category. While other periods could be employed, in the illustrated embodiment the corporate headquarters computer 12 initiates communication with the store computers 40 on a weekly basis. To this end, the system 10 further includes a modem 44, in the corporate headquarters, connected to the corporate headquarters computer 12. The system 10 further includes a modem 46 in each store 42, connected to the store computer 40 of that store 42. Alternative forms of communication, such as dedicated lines, TCP/IP, or satellite communication can be employed.

The system 10 further includes a store printer 48 in each store 42 in communication with the computer 40 of that store. In one embodiment, the printers 48 are laser printers, such as HP3 laser jet printers sold by Hewlett-Packard. The system 10 further includes other typical peripheral computer equipment in the stores, in communication with the computers 40, respectively, such as displays or monitors 50, and data input devices (e.g., keyboards or touch screens) 52.

The store computers 40 are respectively loaded with a label creating computer program for causing the printer to print UPC tags and for causing the printer to print onto labels. The label creating computer program is further capable of performing a logical test to determine if a field has data not equal to a certain value. More particularly, in the illustrated embodiment the computers 40 are loaded with dSign software sold by Access of Seattle, Wash. This software is used by retail industry for creating labels.

The software is customized or programmed so that respective solid black squares 50 are printed in first and second locations 52 and 54 if the product belongs in the green category (FIG. 6), respective solid black squares 50 are printed in the first location 52 and a third location 56 if the product belongs in the yellow category (FIG. 5), and respective solid black squares 50 are printed in the second and third locations 54 and 56 if the product belongs in the red category (FIG. 4), the first, second, and third locations 52, 54, and 56 being spaced apart from one another and being located in a row. Other solid figures, such as solid dots or overstricken characters could be employed in alternative embodiments.

More particularly, the Access software includes a function called a logical test for field with data not equal to a certain value. If a certain field has a value that is not equal to a programmed value, then a value (e.g., text, such as a black box) is put there. This function can be performed for different positions. In the illustrated embodiment, an Adobe font is used to create the black box.

When it is desired to create a label 66, 68, or 70 having category information for a new product, a tag 58 is provided having thereon red, yellow, and green indicia 60, 62, and 64 in a traffic light sequence (FIG. 4). In the illustrated embodiment, the tag 58 includes a black area, indicated by cross hatching, surrounding the red, yellow and green indicia 60, 62, and 64. More particularly, in the illustrated embodiment, the tag 58 is created by GTI, Graphic Technology, which is a label maker that sells its labels across the U.S. The term "yellow", as used in the specification and claims of this patent application, is to be construed as encompassing yellow, amber, or orange, or any shades between yellow, amber, and orange.

The tag 58 is oriented in a store printer 48, and the store computer 40 is caused to execute the label program, so that black squares are printed over the red indicia 60 and the yellow indicia 62 if the product belongs in the green (low fat) category, so that black squares are printed over the yellow indicia 62 and the green indicia 64 if the product belongs in the red (high fat) category, and so that black squares are printed over the red indicia 60 and the green indicia 64 if the product belongs in the yellow (intermediate fat) category. In the illustrated embodiment, pricing information and/or a UPC code are printed at the same time. In this way, the invention can be carried out without the need to use expensive color printers. Instead, lower cost black and white printers, which may already be present can be employed. Cost savings are thus realized.

In an alternative embodiment, instead of obscuring preprinted red, yellow, or green dots, a green dot is printed if the product belongs in the green category, a red dot is printed if the product belongs in the red category, and a yellow dot is printed if the product belongs in the yellow category. This embodiment requires a color printer in one or more of the stores 42.

Optionally, several tags are inserted into the printer in a row (e.g., a roll of perforated tags is sheet fed into the printer 48), and the printer generates a plurality of labels 66, 68, or 70 sequentially. Alternatively, several tags are provided on a single sheet, and such sheets are loaded into a tray of the printer 48, and the printer generates a plurality of labels 66, 68, or 70 simultaneously.

The completed labels 66, 68, or 70 are placed on shelves in the stores 42 adjacent (above or below) the product associated with the labels, which the labels categorize. For example, the labels are placed in locations on the edges of shelves where pricing information is located, and are sized appropriately. In alternative embodiments, the labels 66, 68, or 70 are placed directly on the food products, or used in advertising instead of or in addition to being placed on shelves.

Thus, a system and method has been disclosed which provides consumers with fat quantity information in an easily understood format. No difficult calculations are necessary. No instructions need be provided to the consumers as to how to read the information; consumers intuitively understand the meaning of the labels.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A method of indicating fat content of a food product, the method comprising:

providing a corporate headquarters mainframe computer having a computer program that associates Universal Product Code information with the product, that receives as inputs fat grams and calories per serving for a product, that determines fat percentage by calories for the product, that categorizes the product in a first category if the determined fat percentage by calories is greater than or equal to 50 percent, a second category if the determined fat percentage by calories is between 31 and 49 percent, and a third category if the determined fat percentage by calories is less than or equal to 30 percent, and that associates the category for the product with the Universal Product Code for the product;

providing a plurality of store computers, and a plurality of store printers respectively connected to the store computers, in locations separate from the corporate headquarters computer, the store computers respectively having a label creating computer program for causing the printer to print Universal Product Code tags, and for causing the printer to print onto labels, the label creating computer program further being configured to perform a logical test to determine if a field has data not equal to a certain value;

customizing the respective label creating computer programs so that respective solid black squares are printed in first and second locations if the product belongs in the third category, respective solid black squares are printed in the first location and a third location if the product belongs in the second category, and respective solid black squares are printed in the second and third locations if the product belongs in the first category, the first, second, and third locations being spaced apart from one another and being located in a row;

inputting pricing and nutritional information into the corporate headquarters computer for a product, the nutritional information including separate entries including an entry for fat grams, and an entry for calories per serving;

determining, using the corporate headquarters computer, whether the product falls into the first, second, or third of the categories;

causing the corporate headquarters computer to initiate communications with respective store computers, remote from the corporate headquarters computer, using a dial-up modem connection;

transmitting from the corporate headquarters computer to the store computers Universal Product Code information for the product and the category for the product identified by the Universal Product Code;

providing respective tags having thereon red, yellow, and green indicia in a traffic light sequence; and orienting the tags in respective store printers, and causing the store computers to execute the label program, wherein solid black squares are printed over the red indicia and the yellow indicia if the product belongs in the third category, wherein solid black squares are printed over the red indicia and the green indicia if the product belongs in the second category, and wherein solid black squares are printed over the yellow indicia and the green indicia if the product belongs in the third category.

2. A method of indicating fat content of a food product, the method comprising:

providing a corporate headquarters mainframe computer having a computer program that associates Universal Product Code information with the product, that receives as inputs nutritional information for a product, that determines a percentage of a nutritional parameter provided by the product, that categorizes the product in a first category if the determined percentage is greater than or equal to a first percentage, a second category if the determined percentage is in a range of percentages lower than the first percentage, and a third category if the determined fat percentage is less than or equal to a second percentage lower than the range of percentages, and that associates the category for the product with the Universal Product Code for the product;

providing a plurality of store computers, and a plurality of store printers respectively connected to the store computers, in locations separate from the corporate headquarters computer, the store computers respectively having a label creating computer program for causing the printer to print Universal Product Code tags, for causing the printer to print onto labels, and for performing a logical test to determine if a field has data not equal to a certain value;

customizing the respective label creating computer programs so that an obscuring marking is printed in a first location if the product belongs in the first category, an obscuring marking is printed in a second location if the product belongs in the second category, and an obscuring marking is printed in a third location if the product belongs in the third category;

inputting pricing and nutritional information into the corporate headquarters computer for a product, the nutritional information including separate entries;

determining, using the corporate headquarters computer, whether the product falls into the first, second, or third of the categories;

causing the corporate headquarters computer to initiate communications with respective store computers, remote from the corporate headquarters computer;

transmitting from the corporate headquarters computer to the store computers Universal Product Code information for the product and the category for the product identified by the Universal Product Code;

providing respective tags having thereon graphical indicia, the graphical indicia defining the first, second, and third locations; and orienting the tags in respective store printers, and causing the store computers to execute the label program, wherein the obscuring marking is printed over the first location if the product belongs in the first category, wherein the obscuring marking is printed over the second location if the product belongs in the second category, and wherein the obscuring marking is printed in the third location is the product belongs in the third category.

3. A method of indicating fat content of a food product, the method comprising:

providing a computer having a computer program that associates Universal Product Code information with the product, that receives as inputs nutritional information for a product, that determines a percentage of a nutritional parameter for the product, that categorizes the product in a first category if the determined percentage is greater than or equal to a first percentage, a second category if the determined percentage is in a range of percentages lower than the first percentage, and a third category if the determined percentage is less than or equal to a second percentage lower than the range of percentages, and that associates the category for the product with the Universal Product Code for the product;

providing a printer in communication with the computer;

providing the computer with a label creating computer program for causing the printer to print Universal Product Code tags, for causing the printer to print onto labels, and for performing a logical test to determine if a field has data not equal to a certain value, the label creating computer program being configured to effect printing of an obscuring marking in a first location if the product belongs in the first category, to effect printing of an obscuring marking in a second location if the product belongs in the second category, and to effect printing of an obscuring marking in a third location if the product belongs in the third category;

inputting pricing and nutritional information into the computer for a product, the nutritional information including separate entries;

determining, using the computer, whether the product falls into the first, second, or third of the categories;

providing respective tags having thereon graphical indicia, the graphical indicia defining the first, second, and third locations; and orienting the tags in respective store printers, and causing the computer to execute the label program, wherein the obscuring marking is printed over the first location if the product belongs in the first category, wherein the obscuring marking is printed over the second location if the product belongs in the second category, and wherein the obscuring marking is printed in the third location if the product belongs in the third category.

* * * * *